United States Patent
Le et al.

(10) Patent No.: US 11,437,138 B2
(45) Date of Patent: Sep. 6, 2022

(54) SYSTEM, METHOD, AND COMPUTER PROGRAM PRODUCT FOR TRACKING ENDOSCOPES IN A FORCED-AIR DRYING CABINET

(71) Applicant: Mobile Aspects, Inc., Pittsburgh, PA (US)

(72) Inventors: Khang Nguyen Le, Murrieta, CA (US); Pribadi Kardono, Monroeville, PA (US); Suneil Mandava, Pittsburgh, PA (US); Muhamad Nazaruddin, Monroeville, PA (US); Muhammad R. Rahim, Monroeville, PA (US); Timur P. Sriharto, Monroeville, PA (US)

(73) Assignee: Mobile Aspects, Inc., Pittsburgh, PA (US)

( * ) Notice: Subject to any disclaimer, the term of this patent is extended or adjusted under 35 U.S.C. 154(b) by 517 days.

(21) Appl. No.: 16/591,836

(22) Filed: Oct. 3, 2019

(65) Prior Publication Data
US 2020/0118674 A1    Apr. 16, 2020

Related U.S. Application Data

(60) Provisional application No. 62/745,821, filed on Oct. 15, 2018.

(51) Int. Cl.
*G16H 40/40* (2018.01)
*A61B 1/12* (2006.01)
(Continued)

(52) U.S. Cl.
CPC ......... *G16H 40/40* (2018.01); *A61B 1/00059* (2013.01); *A61B 1/121* (2013.01);
(Continued)

(58) Field of Classification Search
CPC .... G16H 40/40; A61B 1/00059; A61B 1/121; A61B 50/10; A61B 90/70;
(Continued)

(56) References Cited

U.S. PATENT DOCUMENTS

| 8,414,471 B2 | 4/2013 | Mandava et al. |
| 8,992,416 B2 | 3/2015 | Mandava et al. |
| 2018/0000976 A1* | 1/2018 | Nowruzi ................. A61L 2/20 |

FOREIGN PATENT DOCUMENTS

JP    2002282200 A    * 10/2002

OTHER PUBLICATIONS

Pineau, L.; Villard, E.; Duc, D.L.; Marchetti, B. "Endoscope drying/storage cabinet: interest and efficacy." Journal of Hospital Infection68. 1: 59-65. W.B. Saunders Ltd. (Jan. 2008) (Year: 2008).*
(Continued)

*Primary Examiner* — Linh Giang Le
(74) *Attorney, Agent, or Firm* — The Webb Law Firm

(57) ABSTRACT

Described are a system, method, and computer program product for tracking endoscopes in a forced-air drying cabinet including a compressor, a plurality of support arrangements, and an inner area accessible by a door. The method may include receiving a signal from a signal emitting member attached to and associated with an endoscope. The method may also include determining an identifier and a drying protocol of the endoscope. The method may further include identifying a support arrangement to support the endoscope and determining a connection status of the endoscope to a first airflow output and a second airflow output. The method may further include initiating a drying process, when the endoscope is connected, according to the drying protocol by causing the compressor to create at least one airflow through the endoscope from the first airflow output, the second airflow output, or a combination thereof.

20 Claims, 4 Drawing Sheets

(51) Int. Cl.
    *A61B 50/10*     (2016.01)
    *A61B 90/70*     (2016.01)
    *A61B 1/00*     (2006.01)

(52) U.S. Cl.
    CPC .............. *A61B 50/10* (2016.02); *A61B 90/70* (2016.02); *A61B 2050/105* (2016.02); *A61B 2090/701* (2016.02)

(58) Field of Classification Search
    CPC ........ A61B 2050/105; A61B 2090/701; A61B 90/96; A61B 90/98
    See application file for complete search history.

(56) References Cited

OTHER PUBLICATIONS

Endodry Drying and Storage System, May 29, 2018, 1 page, Cantel, http://www.medivators.com/products/endoscope-reprocessing/endoscope-transport-and-storage/endodry-storage-and-drying-system.

Endoscope Drying Cabinet Endoscope Storage Cabinet, Jul. 2, 2015, 4 pages, Medivators, https://www.medivators.com/sites/default/files/minntech/documents/50098-836-EN%20REV%20A%20HR.pdf.

\* cited by examiner

SYSTEM, METHOD, AND COMPUTER PROGRAM PRODUCT FOR TRACKING ENDOSCOPES IN A FORCED-AIR DRYING CABINET

CROSS REFERENCE TO RELATED APPLICATIONS

This application claims priority to U.S. Provisional Patent Application No. 62/745,821, filed Oct. 15, 2018, entitled "System, Method, and Computer Program Product for Tracking Endoscopes in a Forced-Air Drying Cabinet," the entire disclosure of which is hereby incorporated by reference.

BACKGROUND

Technical Field

Disclosed embodiments relate generally to medical device storage arrangements, and in some non-limiting embodiments or aspects, to a system, method, and computer program product for tracking endoscopes within an endoscope storage and drying cabinet, particularly for the tracking, initiation, and verification of reprocessing and drying procedures.

Technical Considerations

Presently, in the health care industry, complex and expensive equipment and systems are utilized in the diagnosis and care process. As the development of this equipment and associated systems continues, the necessity to monitor and track the usage is of the utmost importance. Some medical equipment, such as endoscopes, are expensive and reusable devices that are reprocessed between patient uses. As such, there is a need to track the equipment within and between medical spaces, as well as to verify that the equipment has undergone the appropriate reprocessing. Manual documentation by medical personnel can be both cumbersome and untrustworthy, and the tracking process can become a monumental task due to equipment volume and variety.

Endoscopes, in particular, are subject to a rigorous reprocessing and drying procedure. Reprocessing generally involves the cleaning and sanitizing of the endoscope, which will leave the endoscope in a wet or damp state. Prior to reuse in a procedure, the endoscopes are stored, preferably in a drying cabinet. It would be advantageous if the tracking of endoscopes from one station to another, and within the storage cabinets, were to be automated. Example endoscope storage cabinet tracking systems, and cabinets and tracking devices therein, are described in U.S. Pat. Nos. 8,414,471 and 8,992,416, which are incorporated herein by reference in their entireties.

Hang-drying has drawbacks, principally by being slow and/or imprecise, which may lead to incomplete drying. Incompletely dried endoscopes are more prone to bacterial or fungal growths on stored equipment. Moreover, liquid from within and on hang-dried endoscopes will tend to pool below the bottom outlet of the endoscope, generally on the floor of the cabinet. Some drying cabinets may incorporate ceiling or floor fans to push air through the volume of the cabinet, which helps with the drying process, but this process can be inefficient, as some already dried endoscopes may be continually aired despite not needing further drying.

There is a need in the art for an efficient and automated drying system for inner-endoscope forced-air drying cabinets. In particular, there is a need for a system to automatically track endoscopes around and within drying cabinets, and in particular to track the progress and position of endoscopes in a drying system therein. There is a need for the automated system to automatically determine the position and arrangement of an endoscope in the drying system, particularly based on different endoscope types and varied drying protocols.

SUMMARY

According to some non-limiting embodiments or aspects, provided is an improved system, computer-implemented method, and computer program product for tracking endoscopes in a forced-air drying cabinet. The method may include receiving a signal from a signal emitting member attached to and associated with an endoscope. The method may also include determining an identifier and a drying protocol of the endoscope. The method may further include identifying a support arrangement to support the endoscope and determining a connection status of one or more inner channels of the endoscope to a first airflow output and a second airflow output. The method may further include initiating a drying process, when the endoscope is connected, according to the drying protocol by causing a compressor to create at least one airflow through the endoscope from the first airflow output, the second airflow output, or a combination thereof.

According to some non-limiting embodiments or aspects, provided is a computer-implemented method for tracking at least one endoscope in a forced-air drying cabinet that may include at least one compressor, at least one support arrangement, and an inner area accessible by at least one door. The method may include receiving, with at least one processor, at least one signal from at least one signal emitting member attached to or associated with the at least one endoscope. The method may also include determining, with at least one processor and based at least partially on the at least one signal, at least one identifier of the at least one endoscope. The method may further include determining, with at least one processor, at least one drying protocol for the at least one endoscope based at least partially on the at least one identifier of the at least one endoscope. The at least one drying protocol may include at least one of the following: at least one airflow duration, at least one airflow pressure, at least one airflow speed, at least one airflow temperature, at least one airflow humidity, or any combination thereof. The method may further include identifying, with at least one processor, the at least one support arrangement to support the at least one endoscope. The at least one support arrangement may be associated with at least one first airflow output and at least one second airflow output. The method may further include determining, with at least one processor, at least one connection status indicative of whether at least one first end of the at least one endoscope has been connected to the at least one first airflow output and at least one second end of the at least one endoscope has been connected to the at least one second airflow output. The method may further include, in response to the at least one connection status indicating the at least one endoscope has been connected to the at least one first airflow output and the at least one second airflow output, initiating, with at least one processor, at least one drying process according to the at least one drying protocol for the at least one endoscope by causing the at least one compressor to create at least one airflow through the at least one endoscope from the at least one first airflow output, the at least one second airflow output, or a combination thereof.

In some non-limiting embodiments or aspects, the method may include receiving, with at least one processor, location data of the at least one signal emitting member associated with the at least one endoscope. The method may include, in response to the location data including data of at least one prior detection of the at least one signal emitting member at an endoscope reprocessing system immediately preceding receiving the at least one signal, determining, with at least one processor, that the at least one endoscope has been cleaned. The method may include, in response to the location data not including data of at least one prior detection of the at least one signal emitting member at an endoscope reprocessing system immediately preceding receiving the at least one signal, determining, with at least one processor, that the at least one endoscope has not been cleaned. The method may include, in response to determining that the at least one endoscope was not cleaned, generating, with at least one processor, at least one warning notification at the forced-air drying cabinet. The method may include, in response to determining that the least one endoscope was not cleaned, activating, with at least one processor, at least one locking mechanism of the forced-air drying cabinet to prevent the at least one door from being opened until it is unlocked by a personnel.

In some non-limiting embodiments or aspects, the method may include, prior to initiating the at least one drying protocol for the at least one endoscope, verifying, with at least one processor, that the at least one door is closed. The method may include, in response to determining that the at least one door is open: generating, with at least one processor, at least one notification at the forced-air drying cabinet that the at least one door is open; and waiting to initiate, with at least one processor, the at least one drying protocol for the at least one endoscope until the at least one door is closed.

In some non-limiting embodiments or aspects, the at least one support arrangement may include at least two support arrangements of different configurations associated with at least two different types of endoscope. The identifying the at least one support arrangement may be based at least partially on the at least one identifier of the at least one endoscope and may further include determining, with at least one processor, a configuration of support arrangement required for the at least one endoscope.

In some non-limiting embodiments or aspects, the at least one drying protocol may include the at least one airflow duration. The method may include: tracking, with at least one processor, at least one duration of the at least one endoscope being in the forced-air drying cabinet; and controlling, with at least one processor, at least one time display to provide at least one remaining drying time for the at least one endoscope based at least partially on the at least one airflow duration of the at least one drying protocol in relation to the at least one duration of the at least one endoscope being in the forced-air drying cabinet. The method may include, in response to determining that the at least one duration of the at least one endoscope being in the forced-air drying cabinet satisfies at least one predetermined threshold for the at least one endoscope, generating, with at least one processor, at least one notification at the forced-air drying cabinet identifying the at least one endoscope as requiring reprocessing.

In some non-limiting embodiments or aspects, the forced-air drying cabinet may further include at least one visual indicator associated with the at least one support arrangement. The method may include, in response to identifying the at least one support arrangement to support the at least one endoscope, controlling, with at least one processor, the at least one visual indicator associated with the at least one support arrangement to direct personnel attention to the at least one support arrangement.

In some non-limiting embodiments or aspects, the determining the at least one connection status may include evaluating, with at least one processor, at least one outlet air pressure at the at least one first airflow output associated with the at least one support arrangement identified to support the at least one endoscope and at the at least one second airflow output associated with the at least one support arrangement identified to support the at least one endoscope to at least one predetermined threshold. The method may include, in response to determining that the at least one connection status of the at least one endoscope indicates that the at least one endoscope is not connected, controlling, with at least one processor, the at least one visual indicator associated with the at least one support arrangement to indicate that the at least one endoscope is not connected.

According to non-limiting embodiments or aspects, provided is a system that may include a forced-air drying cabinet including at least one compressor, at least one support arrangement, at least one first airflow output and at least one second airflow output associated with the at least one support arrangement, and an inner area accessible by at least one door. The at least one signal emitting member may be associated with at least one endoscope. The at least one server computer may include at least one processor. The at least one server computer may be configured to receive at least one signal from the at least one signal emitting member. The at least one server computer may also be configured to determine, based at least partially on the at least one signal, at least one identifier of the at least one endoscope. The at least one server computer may further be configured to determine at least one drying protocol for the at least one endoscope based at least partially on the at least one identifier of the at least one endoscope. The at least one drying protocol may include at least one of the following: at least one airflow duration, at least one airflow pressure, at least one airflow speed, at least one airflow temperature, at least one airflow humidity, or any combination thereof. The at least one server computer may be further configured to identify the at least one support arrangement to support the at least one endoscope. The at least one server computer may be further configured to determine at least one connection status indicative of whether at least one first end of the at least one endoscope has been connected to the at least one first airflow output associated with the at least one support arrangement and at least one second end of the at least one endoscope has been connected to the at least one second airflow output associated with the at least one support arrangement. The at least one server computer may be further configured to, in response to the at least one connection status indicating the at least one endoscope has been connected to the at least one first airflow output and the at least one second airflow output associated with the at least one support arrangement, initiate at least one drying process according to the at least one drying protocol for the at least one endoscope by causing the at least one compressor to create at least one airflow through the at least one endoscope from the at least one first airflow output, the at least one second airflow output, or a combination thereof.

In some non-limiting embodiments or aspects, the at least one server computer may be further configured to receive location data of the at least one signal emitting member associated with the at least one endoscope. The at least one server computer may be further configured to, in response to the location data including data of at least one prior detection of the at least one signal emitting member associated with the at least one endoscope at an endoscope reprocessing system immediately preceding receiving the at least one signal, determine that the at least one endoscope has been cleaned. The at least one server computer may be further configured to, in response to the location data not including data of at least one prior detection of the at least one signal emitting member associated with the at least one endoscope at an endoscope reprocessing system immediately preceding receiving the at least one signal, determine that the at least one endoscope has not been cleaned. The at least one server computer may be further configured to, in response to determining that the least one endoscope was not cleaned, generate at least one warning notification at the forced-air drying cabinet. The at least one server computer may be further configured to, in response to determining that the least one endoscope was not cleaned, activate at least one locking mechanism of the forced-air drying cabinet to prevent the at least one door from being opened until it is unlocked by a personnel.

In some non-limiting embodiments or aspects, the at least one server computer may be further configured to, prior to initiating the at least one drying protocol for the at least one endoscope, verify that the at least one door is closed. The at least one server computer may be further configured to, in response to determining that the at least one door is open: generate at least one notification at the forced-air drying cabinet that the at least one door is open; and wait to initiate the at least one drying protocol for the at least one endoscope until the at least one door is closed.

In some non-limiting embodiments or aspects, the at least one support arrangement may include at least two support arrangements of different configurations associated with at least two different types of endoscope. Identifying the at least one support arrangement may be based at least partially on the at least one identifier of the at least one endoscope. The at least one server computer may be further configured to determine a configuration of support arrangement required for the at least one endoscope.

In some non-limiting embodiments or aspects, the at least one drying protocol may include the at least one airflow duration. The at least one server computer may be further configured to: track at least one duration of the at least one endoscope being in the forced-air drying cabinet; and control at least one time display to provide at least one remaining drying time for the at least one endoscope based at least partially on the at least one airflow duration of the at least one drying protocol in relation to the at least one duration of the at least one endoscope being in the forced-air drying cabinet.

In some non-limiting embodiments or aspects, the at least one server computer may be further configured to: in response to determining that the at least one duration of the at least one endoscope being in the forced-air drying cabinet satisfies at least one predetermined threshold for the at least one endoscope, generate at least one notification at the forced-air drying cabinet identifying the at least one endoscope as requiring reprocessing.

In some non-limiting embodiments or aspects, the forced-air drying cabinet may include at least one visual indicator associated with the at least one support arrangement. The at least one server computer may be further configured to, in response to identifying the at least one support arrangement to support the at least one endoscope, control the at least one visual indicator associated with the at least one support arrangement to direct personnel attention to the at least one support arrangement.

In some non-limiting embodiments or aspects, determining the at least one connection status may include evaluating at least one outlet air pressure at the at least one first airflow output associated with the at least one support arrangement identified to support the at least one endoscope and at the at least one second airflow output associated with the at least one support arrangement identified to support the at least one endoscope to at least one predetermined threshold.

In some non-limiting embodiments or aspects, the at least one server computer is further configured to, in response to determining that the at least one connection status of the at least one endoscope indicates that the at least one endoscope is not connected, control the at least one visual indicator associated with the at least one support arrangement identified to support the at least one endoscope to indicate that the at least one endoscope is not connected.

According to non-limiting embodiments or aspects, provided is a computer program product for tracking at least one endoscope in a forced-air drying cabinet having at least one compressor, at least one support arrangement, and an inner area accessible by at least one door. The computer program product may include at least one non-transitory computer-readable medium including program instructions that, when executed by at least one processor, cause the at least one processor to receive at least one signal from at least one signal emitting member associated with the at least one endoscope. The program instructions may cause the at least one processor to determine, based at least partially on the at least one signal, at least one identifier of the at least one endoscope. The program instructions may also cause the at least one processor to determine at least one drying protocol for the at least one endoscope based at least partially on the at least one identifier of the at least one endoscope, the at least one drying protocol including at least one of the following: at least one airflow duration, at least one airflow pressure, at least one airflow speed, at least one airflow temperature, at least one airflow humidity, or any combination thereof. The program instructions may further cause the at least one processor to identify the at least one support arrangement to support the at least one endoscope. The at least one support arrangement may be associated with at least one first airflow output and at least one second airflow output. The program instructions may further cause the at least one processor to determine at least one connection status indicative of whether at least one first end of the at least one endoscope has been connected to the at least one first airflow output and at least one second end of the at least one endoscope has been connected to the at least one second airflow output. The program instructions may further cause the at least one processor to, in response to the at least one connection status indicating the at least one endoscope has been connected to the at least one first airflow output and the at least one second airflow output, initiate at least one drying process according to the at least one drying protocol for the at least one endoscope by causing the at least one compressor to create at least one airflow through the at least one endoscope from the at least one first airflow output, the at least one second airflow output, or a combination thereof.

In some non-limiting embodiments or aspects, the program instructions may cause the at least one processor to receive location data of the at least one signal emitting member associated with the at least one endoscope. The program instructions may cause the at least one processor to, in response to the location data including data of at least one prior detection of the at least one signal emitting member associated with the at least one endoscope at an endoscope reprocessing system immediately preceding receiving the at least one signal, determine that the at least one endoscope has been cleaned. The program instructions may cause the at least one processor to, in response to the location data not including data of at least one prior detection of the at least one signal emitting member associated with the at least one endoscope at an endoscope reprocessing system immediately preceding receiving the at least one signal, determine that the at least one endoscope has not been cleaned. The program instructions may cause the at least one processor to, in response to determining that the at least one endoscope was not cleaned, generate at least one warning notification at the forced-air drying cabinet. The program instructions may cause the at least one processor to, in response to determining that the least one endoscope was not cleaned, activate at least one locking mechanism of the forced-air drying cabinet to prevent the at least one door from being opened until it is unlocked by a personnel.

In some non-limiting embodiments or aspects, the program instructions may cause the at least one processor to, prior to initiating the at least one drying protocol for the at least one endoscope, verify that the at least one door is closed. The program instructions may cause the at least one processor to, in response to determining that the at least one door is open: generate at least one notification at the forced-air drying cabinet that the at least one door is open; and wait to initiate the at least one drying protocol for the at least one endoscope until the at least one door is closed.

In some non-limiting embodiments or aspects, the at least one support arrangement may include at least two support arrangements of different configurations associated with at least two different types of endoscope. Identifying the at least one support arrangement may be based at least partially on the at least one identifier of the at least one endoscope. The program instructions may cause the at least one processor to determine a configuration of support arrangement required for the at least one endoscope.

In some non-limiting embodiments or aspects, the at least one drying protocol may include the at least one airflow duration. The program instructions may cause the at least one processor to: track at least one duration of the at least one endoscope being in the forced-air drying cabinet; and control at least one time display to provide at least one remaining drying time for the at least one endoscope based at least partially on the at least one airflow duration of the at least one drying protocol in relation to the at least one duration of the at least one endoscope being in the forced-air drying cabinet.

In some non-limiting embodiments or aspects, The program instructions may cause the at least one processor to, in response to determining that the at least one duration of the at least one endoscope being in the forced-air drying cabinet satisfies at least one predetermined threshold for the at least one endoscope, generate at least one notification at the forced-air drying cabinet identifying the at least one endoscope as requiring reprocessing.

In some non-limiting embodiments or aspects, the forced-air drying cabinet may include at least one visual indicator associated with the at least one support arrangement. The program instructions may cause the at least one processor to, in response to identifying the at least one support arrangement to support the at least one endoscope, control the at least one visual indicator associated with the at least one support arrangement to direct personnel attention to the at least one support arrangement.

In some non-limiting embodiments or aspects, determining the at least one connection status may include evaluating at least one outlet air pressure at the at least one first airflow output associated with the at least one support arrangement identified to support the at least one endoscope and at the at least one second airflow output associated with the at least one support arrangement identified to support the at least one endoscope to at least one predetermined threshold.

In some non-limiting embodiments or aspects, the program instructions may cause the at least one processor to, in response to determining that the at least one connection status of the at least one endoscope indicates that the at least one endoscope is not connected, control the at least one visual indicator associated with the at least one support arrangement identified to support the at least one endoscope to indicate that the at least one endoscope is not connected.

Further non-limiting embodiments or aspects of the present disclosure will be set forth in the following numbered clauses:

Clause 1: A computer-implemented method for tracking at least one endoscope in a forced-air drying cabinet comprising at least one compressor, at least one support arrangement, and an inner area accessible by at least one door, the method comprising: receiving, with at least one processor, at least one signal from at least one signal emitting member attached to or associated with the at least one endoscope; determining, with at least one processor and based at least partially on the at least one signal, at least one identifier of the at least one endoscope; determining, with at least one processor, at least one drying protocol for the at least one endoscope based at least partially on the at least one identifier of the at least one endoscope, the at least one drying protocol comprising at least one of the following: at least one airflow duration, at least one airflow pressure, at least one airflow speed, at least one airflow temperature, at least one airflow humidity, or any combination thereof; identifying, with at least one processor, the at least one support arrangement to support the at least one endoscope, the at least one support arrangement associated with at least one first airflow output and at least one second airflow output; determining, with at least one processor, at least one connection status indicative of whether at least one first end of the at least one endoscope has been connected to the at least one first airflow output and at least one second end of the at least one endoscope has been connected to the at least one second airflow output; and, in response to the at least one connection status indicating the at least one endoscope has been connected to the at least one first airflow output and the at least one second airflow output, initiating, with at least one processor, at least one drying process according to the at least one drying protocol for the at least one endoscope by causing the at least one compressor to create at least one airflow through the at least one endoscope from the at least one first airflow output, the at least one second airflow output, or a combination thereof.

Clause 2: The computer-implemented method of clause 1, further comprising: receiving, with at least one processor, location data of the at least one signal emitting member associated with the at least one endoscope; in response to the location data comprising data of at least one prior detection of the at least one signal emitting member at an endoscope reprocessing system immediately preceding receiving the at least one signal, determining, with at least one processor, that the at least one endoscope has been cleaned; and, in response to the location data not comprising data of at least one prior detection of the at least one signal emitting member at an endoscope reprocessing system immediately preceding receiving the at least one signal, determining, with at least one processor, that the at least one endoscope has not been cleaned.

Clause 3: The computer-implemented method of clause 1 or 2, further comprising, in response to determining that the at least one endoscope was not cleaned, generating, with at least one processor, at least one warning notification at the forced-air drying cabinet.

Clause 4: The computer-implemented method of any of clauses 1-3, further comprising, in response to determining that the least one endoscope was not cleaned, activating, with at least one processor, at least one locking mechanism of the forced-air drying cabinet to prevent the at least one door from being opened until it is unlocked by a personnel.

Clause 5: The computer-implemented method of any of clauses 1-4, further comprising prior to initiating the at least one drying protocol for the at least one endoscope, verifying, with at least one processor, that the at least one door is closed.

Clause 6: The computer-implemented method of any of clauses 1-5, further comprising, in response to determining that the at least one door is open: generating, with at least one processor, at least one notification at the forced-air drying cabinet that the at least one door is open; and waiting to initiate, with at least one processor, the at least one drying protocol for the at least one endoscope until the at least one door is closed.

Clause 7: The computer-implemented method of any of clauses 1-6, wherein the at least one support arrangement comprises at least two support arrangements of different configurations associated with at least two different types of endoscope, and wherein the identifying the at least one support arrangement is based at least partially on the at least one identifier of the at least one endoscope and further comprises determining, with at least one processor, a configuration of support arrangement required for the at least one endoscope.

Clause 8: The computer-implemented method of any of clauses 1-7, wherein the at least one drying protocol comprises the at least one airflow duration, the method further comprising: tracking, with at least one processor, at least one duration of the at least one endoscope being in the forced-air drying cabinet; and controlling, with at least one processor, at least one time display to provide at least one remaining drying time for the at least one endoscope based at least partially on the at least one airflow duration of the at least one drying protocol in relation to the at least one duration of the at least one endoscope being in the forced-air drying cabinet.

Clause 9: The computer-implemented method of any of clauses 1-8, further comprising: in response to determining that the at least one duration of the at least one endoscope being in the forced-air drying cabinet satisfies at least one predetermined threshold for the at least one endoscope, generating, with at least one processor, at least one notification at the forced-air drying cabinet identifying the at least one endoscope as requiring reprocessing.

Clause 10: The computer-implemented method of any of clauses 1-9, wherein the forced-air drying cabinet further comprises at least one visual indicator associated with the at least one support arrangement, the method further comprising: in response to identifying the at least one support arrangement to support the at least one endoscope, controlling, with at least one processor, the at least one visual indicator associated with the at least one support arrangement to direct personnel attention to the at least one support arrangement.

Clause 11: The computer-implemented method of any of clauses 1-10, wherein the determining the at least one connection status comprises evaluating, with at least one processor, at least one outlet air pressure at the at least one first airflow output associated with the at least one support arrangement identified to support the at least one endoscope and at the at least one second airflow output associated with the at least one support arrangement identified to support the at least one endoscope to at least one predetermined threshold.

Clause 12: The computer-implemented method of any of clauses 1-11, further comprising, in response to determining that the at least one connection status of the at least one endoscope indicates that the at least one endoscope is not connected, controlling, with at least one processor, the at least one visual indicator associated with the at least one support arrangement to indicate that the at least one endoscope is not connected.

Clause 13: A system comprising: a forced-air drying cabinet comprising at least one compressor, at least one support arrangement, at least one first airflow output and at least one second airflow output associated with the at least one support arrangement, and an inner area accessible by at least one door; at least one signal emitting member associated with at least one endoscope; at least one server computer comprising at least one processor, the at least one server computer configured to: receive at least one signal from the at least one signal emitting member; determine, based at least partially on the at least one signal, at least one identifier of the at least one endoscope; determine at least one drying protocol for the at least one endoscope based at least partially on the at least one identifier of the at least one endoscope, the at least one drying protocol comprising at least one of the following: at least one airflow duration, at least one airflow pressure, at least one airflow speed, at least one airflow temperature, at least one airflow humidity, or any combination thereof; identify the at least one support arrangement to support the at least one endoscope; determine at least one connection status indicative of whether at least one first end of the at least one endoscope has been connected to the at least one first airflow output associated with the at least one support arrangement and at least one second end of the at least one endoscope has been connected to the at least one second airflow output associated with the at least one support arrangement; and in response to the at least one connection status indicating the at least one endoscope has been connected to the at least one first airflow output and the at least one second airflow output associated with the at least one support arrangement, initiate at least one drying process according to the at least one drying protocol for the at least one endoscope by causing the at least one compressor to create at least one airflow through the at least one endoscope from the at least one first airflow output, the at least one second airflow output, or a combination thereof.

Clause 14: The system of clause 13, wherein the at least one server computer is further configured to: receive location data of the at least one signal emitting member associated with the at least one endoscope; in response to the location data comprising data of at least one prior detection of the at least one signal emitting member associated with the at least one endoscope at an endoscope reprocessing system immediately preceding receiving the at least one signal, determine that the at least one endoscope has been cleaned; and, in response to the location data not comprising data of at least one prior detection of the at least one signal emitting member associated with the at least one endoscope at an endoscope reprocessing system immediately preceding receiving the at least one signal, determine that the at least one endoscope has not been cleaned.

Clause 15: The system of clause 13 or 14, wherein the at least one server computer is further configured to, in response to determining that the least one endoscope was not cleaned, generate at least one warning notification at the forced-air drying cabinet.

Clause 16: The system of any of clauses 13-15, wherein the at least one server computer is further configured to, in response to determining that the least one endoscope was not cleaned, activate at least one locking mechanism of the forced-air drying cabinet to prevent the at least one door from being opened until it is unlocked by a personnel.

Clause 17: The system of any of clauses 13-16, wherein the at least one server computer is further configured to, prior to initiating the at least one drying protocol for the at least one endoscope, verify that the at least one door is closed.

Clause 18: The system of any of clauses 13-17, wherein the at least one server computer is further configured to, in response to determining that the at least one door is open: generate at least one notification at the forced-air drying cabinet that the at least one door is open; and wait to initiate the at least one drying protocol for the at least one endoscope until the at least one door is closed.

Clause 19: The system of any of clauses 13-18, wherein the at least one support arrangement comprises at least two support arrangements of different configurations associated with at least two different types of endoscope, wherein identifying the at least one support arrangement is based at least partially on the at least one identifier of the at least one endoscope, and wherein the at least one server computer is further configured to determine a configuration of support arrangement required for the at least one endoscope.

Clause 20: The system of any of clauses 13-19, wherein the at least one drying protocol comprises the at least one airflow duration, and wherein the at least one server computer is further configured to: track at least one duration of the at least one endoscope being in the forced-air drying cabinet; and control at least one time display to provide at least one remaining drying time for the at least one endoscope based at least partially on the at least one airflow duration of the at least one drying protocol in relation to the at least one duration of the at least one endoscope being in the forced-air drying cabinet.

Clause 21: The system of any of clauses 13-20, wherein the at least one server computer is further configured to: in response to determining that the at least one duration of the at least one endoscope being in the forced-air drying cabinet satisfies at least one predetermined threshold for the at least one endoscope, generate at least one notification at the forced-air drying cabinet identifying the at least one endoscope as requiring reprocessing.

Clause 22: The system of any of clauses 13-21, wherein the forced-air drying cabinet further comprises at least one visual indicator associated with the at least one support arrangement, and the at least one server computer is further configured to: in response to identifying the at least one support arrangement to support the at least one endoscope, control the at least one visual indicator associated with the at least one support arrangement to direct personnel attention to the at least one support arrangement.

Clause 23: The system of any of clauses 13-22, wherein determining the at least one connection status comprises evaluating at least one outlet air pressure at the at least one first airflow output associated with the at least one support arrangement identified to support the at least one endoscope and at the at least one second airflow output associated with the at least one support arrangement identified to support the at least one endoscope to at least one predetermined threshold.

Clause 24: The system of any of clauses 13-23, wherein the at least one server computer is further configured to, in response to determining that the at least one connection status of the at least one endoscope indicates that the at least one endoscope is not connected, control the at least one visual indicator associated with the at least one support arrangement identified to support the at least one endoscope to indicate that the at least one endoscope is not connected.

Clause 25: A computer program product for tracking at least one endoscope in a forced-air drying cabinet comprising at least one compressor, at least one support arrangement, and an inner area accessible by at least one door, the computer program product comprising at least one non-transitory computer-readable medium including program instructions that, when executed by at least one processor, cause the at least one processor to: receive at least one signal from at least one signal emitting member associated with the at least one endoscope; determine, based at least partially on the at least one signal, at least one identifier of the at least one endoscope; determine at least one drying protocol for the at least one endoscope based at least partially on the at least one identifier of the at least one endoscope, the at least one drying protocol comprising at least one of the following: at least one airflow duration, at least one airflow pressure, at least one airflow speed, at least one airflow temperature, at least one airflow humidity, or any combination thereof; identify the at least one support arrangement to support the at least one endoscope, the at least one support arrangement associated with at least one first airflow output and at least one second airflow output; determine at least one connection status indicative of whether at least one first end of the at least one endoscope has been connected to the at least one first airflow output and at least one second end of the at least one endoscope has been connected to the at least one second airflow output; and, in response to the at least one connection status indicating the at least one endoscope has been connected to the at least one first airflow output and the at least one second airflow output, initiate at least one drying process according to the at least one drying protocol for the at least one endoscope by causing the at least one compressor to create at least one airflow through the at least one endoscope from the at least one first airflow output, the at least one second airflow output, or a combination thereof.

Clause 26: The computer program product of clause 25, wherein the program instructions further cause the at least one processor to: receive location data of the at least one signal emitting member associated with the at least one endoscope; in response to the location data comprising data of at least one prior detection of the at least one signal emitting member associated with the at least one endoscope at an endoscope reprocessing system immediately preceding receiving the at least one signal, determine that the at least one endoscope has been cleaned; and, in response to the location data not comprising data of at least one prior detection of the at least one signal emitting member associated with the at least one endoscope at an endoscope reprocessing system immediately preceding receiving the at least one signal, determine that the at least one endoscope has not been cleaned.

Clause 27: The computer program product of clause 25 or 26, wherein the program instructions further cause the at least one processor to, in response to determining that the at least one endoscope was not cleaned, generate at least one warning notification at the forced-air drying cabinet.

Clause 28: The computer program product of any of clauses 25-27, wherein the program instructions further cause the at least one processor to, in response to determining that the least one endoscope was not cleaned, activate at least one locking mechanism of the forced-air drying cabinet to prevent the at least one door from being opened until it is unlocked by a personnel.

Clause 29: The computer program product of any of clauses 25-28, wherein the program instructions further cause the at least one processor to, prior to initiating the at least one drying protocol for the at least one endoscope, verify that the at least one door is closed.

Clause 30: The computer program product of any of clauses 25-29, wherein the program instructions further cause the at least one processor to, in response to determining that the at least one door is open: generate at least one notification at the forced-air drying cabinet that the at least one door is open; and wait to initiate the at least one drying protocol for the at least one endoscope until the at least one door is closed.

Clause 31: The computer program product of any of clauses 25-30, wherein the at least one support arrangement comprises at least two support arrangements of different configurations associated with at least two different types of endoscope, wherein identifying the at least one support arrangement is based at least partially on the at least one identifier of the at least one endoscope, and wherein the program instructions further cause the at least one processor to determine a configuration of support arrangement required for the at least one endoscope.

Clause 32: The computer program product of any of clauses 25-31, wherein the at least one drying protocol comprises the at least one airflow duration, and wherein the program instructions further cause the at least one processor to: track at least one duration of the at least one endoscope being in the forced-air drying cabinet; and control at least one time display to provide at least one remaining drying time for the at least one endoscope based at least partially on the at least one airflow duration of the at least one drying protocol in relation to the at least one duration of the at least one endoscope being in the forced-air drying cabinet.

Clause 33: The computer program product of any of clauses 25-32, wherein the program instructions further cause the at least one processor to: in response to determining that the at least one duration of the at least one endoscope being in the forced-air drying cabinet satisfies at least one predetermined threshold for the at least one endoscope, generate at least one notification at the forced-air drying cabinet identifying the at least one endoscope as requiring reprocessing.

Clause 34: The computer program product of any of clauses 25-33, wherein the forced-air drying cabinet further comprises at least one visual indicator associated with the at least one support arrangement, and the program instructions further cause the at least one processor to: in response to identifying the at least one support arrangement to support the at least one endoscope, control the at least one visual indicator associated with the at least one support arrangement to direct personnel attention to the at least one support arrangement.

Clause 35: The computer program product of any of clauses 25-34, wherein determining the at least one connection status comprises evaluating at least one outlet air pressure at the at least one first airflow output associated with the at least one support arrangement identified to support the at least one endoscope and at the at least one second airflow output associated with the at least one support arrangement identified to support the at least one endoscope to at least one predetermined threshold.

Clause 36: The computer program product of any of clauses 25-35, wherein the program instructions further cause the at least one processor to, in response to determining that the at least one connection status of the at least one endoscope indicates that the at least one endoscope is not connected, control the at least one visual indicator associated with the at least one support arrangement identified to support the at least one endoscope to indicate that the at least one endoscope is not connected.

These and other features and characteristics of the present disclosure, as well as the methods of operation and functions of the related elements of structures and the combination of parts and economies of manufacture, will become more apparent upon consideration of the following description, and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure. As used in the specification and the claims, the singular forms of "a," "an," and "the" include plural referents unless the context clearly dictates otherwise.

BRIEF DESCRIPTION OF THE DRAWINGS

Additional advantages and details of the disclosure are explained in greater detail below with reference to the exemplary embodiments that are illustrated in the accompanying figures, in which.

DETAILED DESCRIPTION

Figure 1:
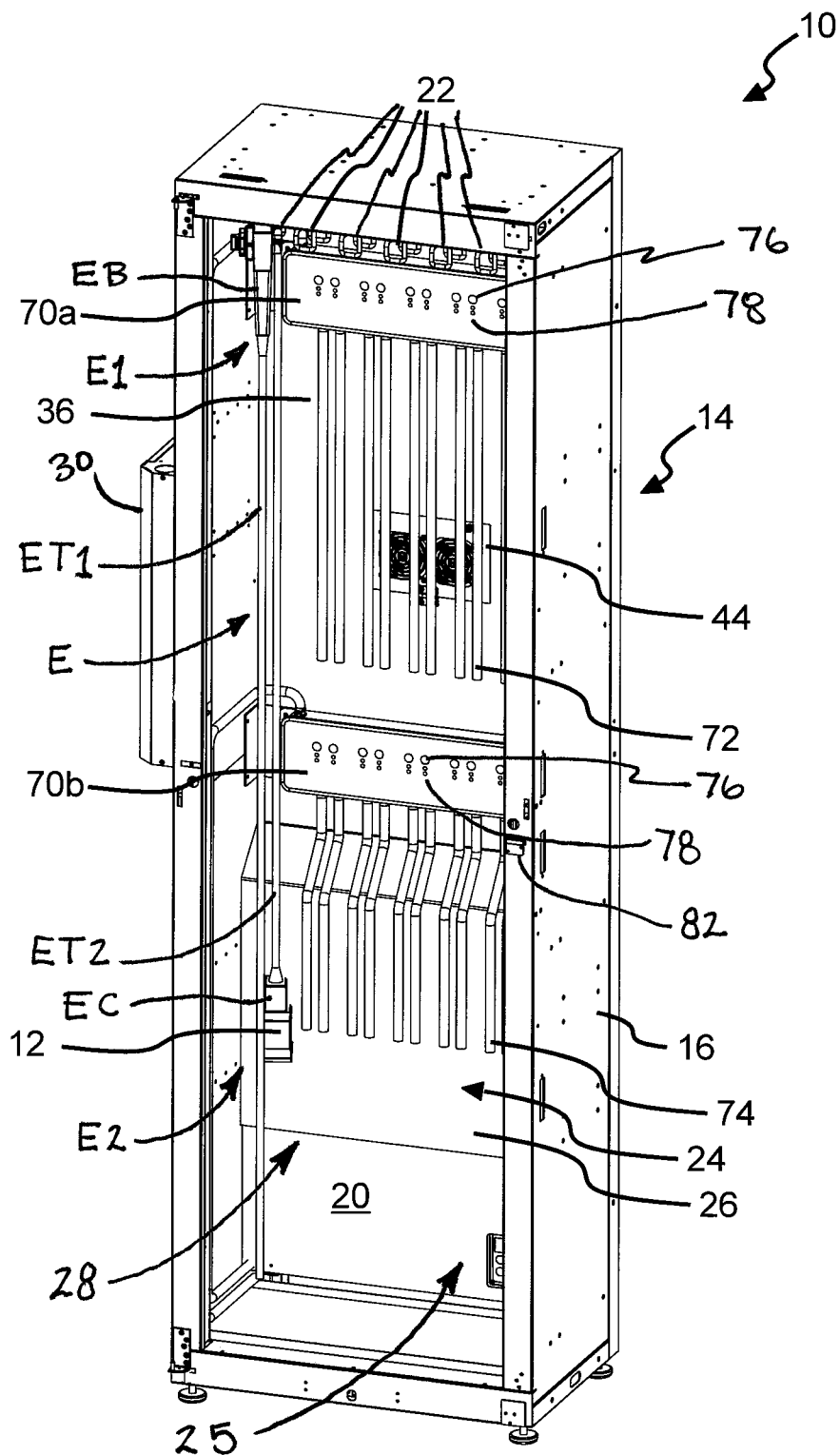
FIG. 1 is a schematic diagram of one non-limiting embodiment or aspect of a system and method for tracking endoscopes in a forced-air drying cabinet.
Figure 2:
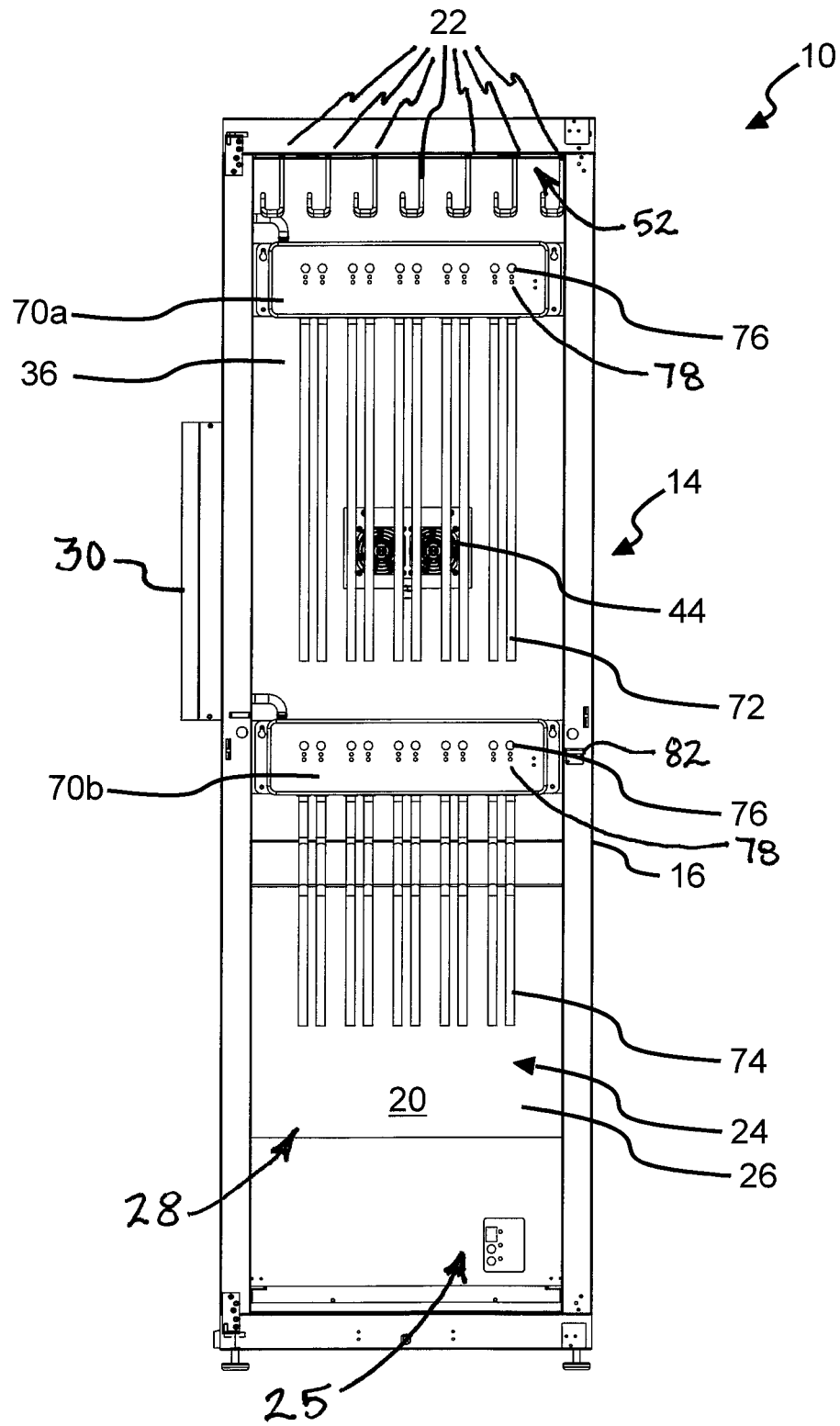
FIG. 2 is a schematic diagram of one non-limiting embodiment or aspect of a system and method for tracking endoscopes in a forced-air drying cabinet.
Figure 3:
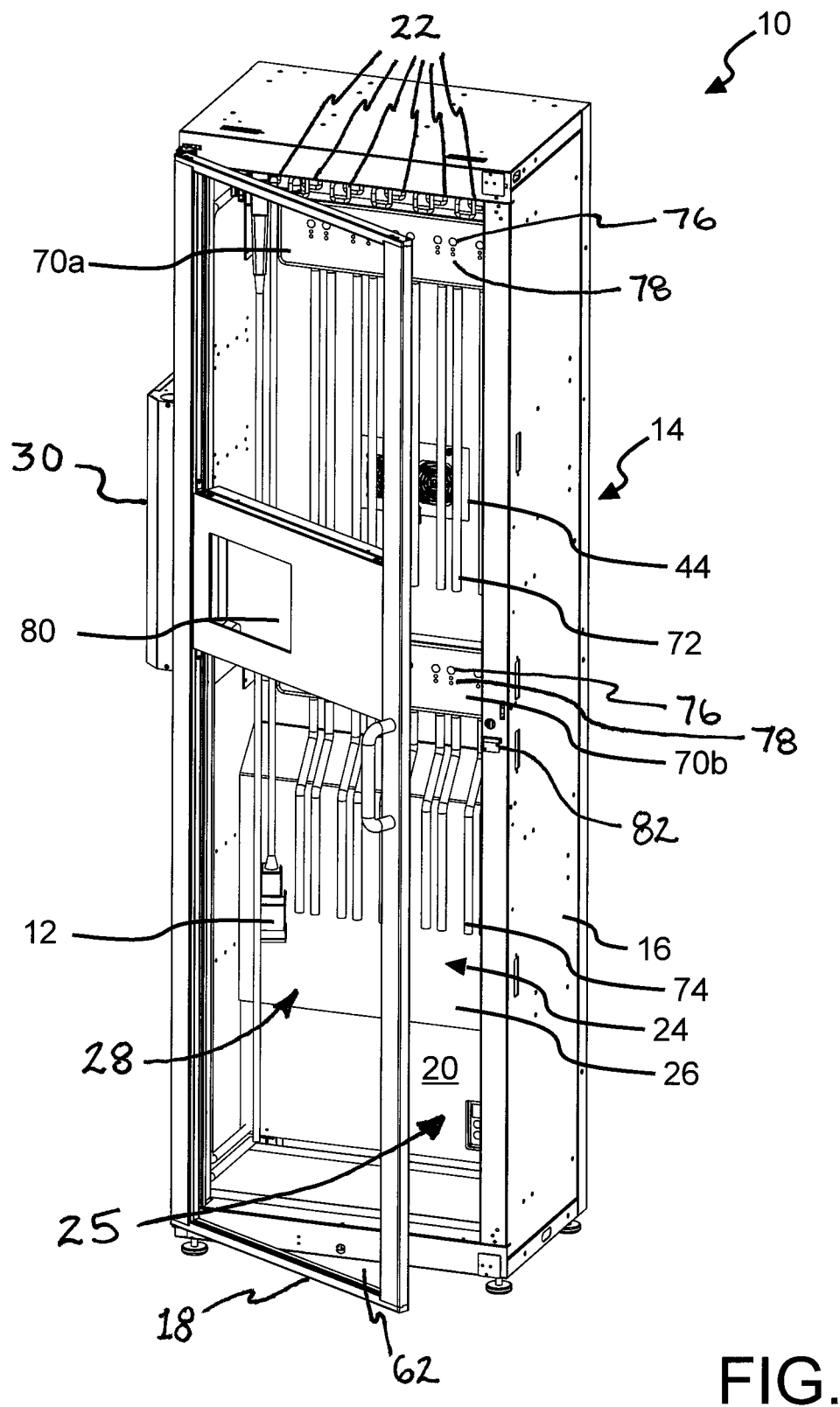
FIG. 3 is a schematic diagram of one non-limiting embodiment or aspect of a system and method for tracking endoscopes in a forced-air drying cabinet.
Figure 4:
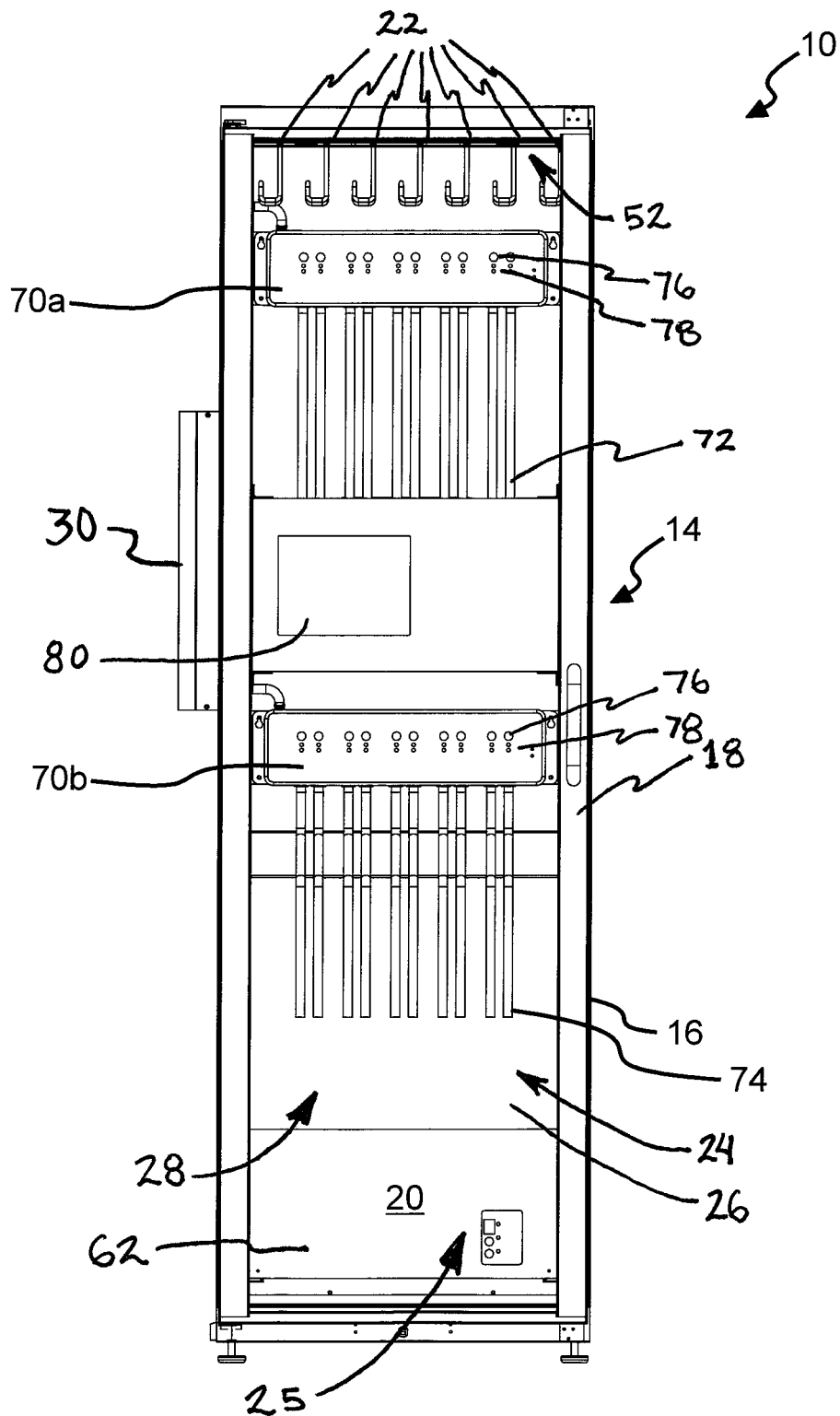
FIG. 4 is a schematic diagram of one non-limiting embodiment or aspect of a system and method for tracking endoscopes in a forced-air drying cabinet.

For purposes of the description hereinafter, the terms "upper", "lower", "right", "left", "vertical", "horizontal", "top", "bottom", "lateral", "longitudinal," and derivatives thereof shall relate to non-limiting embodiments as they are oriented in the drawing figures. However, it is to be understood that the non-limiting embodiments may assume various alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting. Also, it should be understood that any numerical range recited herein is intended to include all sub-ranges subsumed therein. For example, a range of 1 to 10 is intended to include all sub-ranges between (and including) the recited minimum value of 1 and the recited maximum value of 10, that is, having a minimum value equal to or greater than 1 and a maximum value of equal to or less than 10.

As used herein, the terms "communication" and "communicate" refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other, even though the data transmitted may be modified, processed, relayed, and/or routed between the first and second unit. For example, a first unit may be in communication with a second unit, even though the first unit passively receives data and does not actively transmit data to the second unit. As another example, a first unit may be in communication with a second unit if an intermediary unit processes data from one unit and transmits processed data to the second unit.

As used herein, the term "mobile device" may refer to one or more portable electronic devices configured to communicate with one or more networks. As an example, a mobile device may include a cellular phone (e.g., a smartphone or standard cellular phone), a portable computer (e.g., a tablet computer, a laptop computer, etc.), a wearable device (e.g., a watch, pair of glasses, lens, clothing, and/or the like), a personal digital assistant (PDA), and/or other like devices.

As used herein, the term "server" may refer to or include one or more processors or computers, storage devices, or similar computer arrangements that are operated by or facilitate communication and processing for multiple parties in a network environment, such as the internet. In some non-limiting embodiments or aspects, communication may be facilitated over one or more public or private network environments and that various other arrangements are possible. Further, multiple computers, e.g., servers, or other computerized devices, e.g., mobile devices, directly or indirectly communicating in the network environment may constitute a system, such as a hospital storage monitoring system. Reference to a server or a processor, as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function. A server that is "configured" to perform the one or more steps of a process may be understood to refer to either hardware or software configurations, such as programming, network connections, and/or the like.

As used herein, the term "identifier" may refer to any electronic means of identifying an object, process, place, or other parameter thereof. An identifier may be an attribute, number, string, token, analog signal, digital signal, and/or the like. It will be appreciated that many variations are possible.

As used herein, the term "endoscope" may refer to an instrument that can be introduced into the body to give a view of its internal parts. For example, an endoscope may be an optical instrument with a slender, tubular form.

As used herein, the term "reprocessing," in relation to endoscopes, may refer to a cleaning and/or treatment process that is useful for ultimately rendering the endoscope disinfected and ready for reuse. "Reprocessing systems" may include machines and/or processes that provide for reprocessing of endoscopes. Reprocessing systems may provide any number of steps, including, but not limited to pre-cleaning (e.g., rinsing with a fluid after an endoscopic procedure to prevent the formation of biofilm), leak-testing (e.g., introducing a fluid to detect any damage to external surfaces or internal channels that may result in inadequate disinfection or damage to an endoscope), cleaning (e.g., brushing and flushing of channels and ports, such as to remove residual organic material), inspection (e.g., visually determining that the endoscope is clean and free of defects), and disinfection/sterilization (e.g., introducing chemicals or sterilants, such as through automated endoscope reprocessors).

In some non-limiting embodiments or aspects, the present disclosure is directed to a system, method, and computer program product for tracking and managing medical equipment, namely endoscopes, in a forced-air drying cabinet. The present disclosure provides advantages over the prior art by automatically determining endoscope types and appropriate storage arrangements based on the endoscope type. In this manner, endoscopes will be connected and hung in arrangements deemed most efficient for the drying of the endoscope, reducing drying time, energy consumption, and likelihood of bacterial or fungal growth. Moreover, the present disclosure provides for the automatic determination of drying protocols for various types of endoscopes, based on one or more customizable parameters for the forced-air drying systems, and such protocols can be initiated and controlled based on the placement of the endoscope within the cabinet, again realizing energy and time savings. Scopes will, therefore, not be over-or under-dried. Furthermore, due to the advantages of tracking the equipment both in and outside of the cabinet, the systems can identify unclean scopes or identify scopes that have been stored for too long and, therefore, need reprocessing. Many advantages are provided by the present disclosure herein, including those described further below.

The present disclosure is directed to a storage cabinet and tracking system for use in connection with medical devices, e.g., an endoscope E. As is known, an endoscope E may include a first end E1 and a second end E2. The first end E1 of the endoscope E may include a main body EB, with an insertion tube ET1 and a connecting tube ET2 extending therefrom. The connecting tube ET2 connects and allows communication, e.g., electrical communication, between the main body EB (or its internal electrical components) and a light source connector EC, which is located at the second end E2 of the endoscope E. The remaining electrical components and configuration of the endoscope E are well known in the art and the field of medical diagnostic systems.

With specific reference to FIG. 1, and in some non-limiting embodiments or aspects, provided is an endoscope storage cabinet 10. The depicted endoscope storage cabinet 10 is configured or adapted for use in connection with at least one endoscope E having at least one signal emitting member 12 attached to or associated therewith. The signal emitting member 12 is configured to emit a signal indicative of at least one attribute of the endoscope E to which it is attached or associated. For example, the signal may indicate an endoscope identifier such as a serial number, a unique token, a scope type, a drying protocol identifier, and/or the like. Further, the signal emitting member 12 may be in the form of a tag, a transponder, a chip, or other signal emitting component capable of emitting a signal that carries data, preferably data associated with the item to which it is attached, i.e., the endoscope E. While, as discussed hereinafter, in some non-limiting embodiments or aspects, the signal emitting member 12 is a radio frequency emitting device, it is envisioned that any emission/receiving structure, arrangement, and system can be utilized without departing from the spirit or scope of the present disclosure.

With specific reference to FIGS. 1-4, and in some non-limiting embodiments or aspects, the storage cabinet 10 may include an enclosed structure 14 formed by walls 16 (upper, lower, and side) and a door 18. By using the door 18, one has access to an inner area 20 of the cabinet 10. Of course, in place of the door 18, any access structure can be used, such as a panel, a sliding panel, a drawer, or the like. In the inner area 20 and attached directly or indirectly to at least one of the walls 16 is at least one (and preferably multiple) support arrangements 22 for supporting at least a portion of an endoscope E positioned thereon. Preferably, the support arrangements 22 are designed to support the endoscope E at its first end E1 by making at least partial contact with the main body EB and the insertion tube ET1.

With specific reference to FIGS. 1-4, and in some non-limiting embodiments or aspects, the storage cabinet 10 may further include at least one signal receiving device 24 that is attached to or associated with the enclosed structure 14 and utilized to receive the signal emitted from the signal emitting member 12 (attached to the endoscope E). In some non-limiting embodiments or aspects, the signal receiving device 24 is a planar antenna 26 structure that is positioned at or near a lower area 28 of the enclosed structure 14. It will be appreciated that the planar antenna 26 also may be located elsewhere in the cabinet 10, such as on or in the floor, the walls 16, or the ceiling. Two or more antenna 26 may be provided and may be associated with one or more endoscopes E supported by respective support arrangements 22. In addition, a local control device 30, e.g., a control processor, may be attached to, associated with, or integrated within the storage cabinet 10, and this local control device 30 may be in communication with the signal receiving devices 24 and used to receive and process the signals emitted by the signal emitting members 12. It will be appreciated that the local control device 30 may be positioned on, in, or nearby the cabinet 10 provided with a communicative connection to the electronics therein.

With specific reference to FIGS. 1-4, and in some non-limiting embodiments or aspects, the local control device 30 may include a variety of electrical components, circuit boards, storage medium, computing devices, and/or the like for receiving and processing signals and other data streams. Therefore, the local control device 30 may take a variety of forms. In one non-limiting embodiment, the local control device 30 may include a processor or other computing means, as well as a temporary or permanent storage medium for executing program instructions and otherwise implementing the embedded, loaded, or received software code. In addition, this local control device 30 may be used to interface with and/or control other electrical components and sub-systems within the cabinet 10. It will be appreciated that many configurations are possible.

With specific reference to FIGS. 1-4, and in some non-limiting embodiments or aspects, the door 18 may be locked by at least one locking arrangement that is in direct or indirect communication with the local control device 30. For example, the cabinet 10 may be locked with an electrically-operated lock, actuated through application software embedded, or loaded on the local control device 30, thereby providing physical security and preventing access to the inner area 20 of the cabinet 10. This locking arrangement can be "defeated" with a key-operated, manual override, if necessary. Otherwise, and as discussed hereinafter, some interface device can be provided to allow restricted user access based upon user identification, authority levels, authentication systems, and the like. Further, the locking arrangement may be controlled remotely by or through a central control device or remote computer.

With specific reference to FIGS. 1-4, and in some non-limiting embodiments or aspects, the support arrangement 22 may be in the form of projecting members, which extend from an inner surface of a wall 16 of the enclosed structure 14. These projecting members may also be attached to the wall 16 indirectly by first attaching a bracket to the wall 16, and the projecting members to the bracket. Further, in the depicted non-limiting embodiment, multiple support arrangements 22 are included, and each of these support arrangements 22 include a set of projecting members. It is further envisioned that some local locking device or arrangement can be used in connection with each support arrangement 22 to provide additional security. For example, each of these local locking arrangements could be electrically operated by or through the local control device 30, thereby only selectively allowing certain endoscopes E within the cabinet 10 to be inserted or removed.

With specific reference to FIGS. 1-4, and in some non-limiting embodiments or aspects, one or more light members 52 can be provided, such as in the form of overhead lighting (e.g., light bars, light bulbs, LEDs, etc.) in the inner area 20 of the cabinet 10. In this embodiment, these light members 52 are managed through the software or other program instructions on the local control device 30, or other electrical component in the storage cabinet 10. For example, these light members 52 may be colored lights, e.g., red lights that are turned on to indicate a problem within the cabinet 10, or otherwise indicate some issue within the cabinet 10 or with the endoscopes E positioned in the cabinet 10. Still further, and as discussed, the electrical components can be situated above the enclosed structure 14 in a housing, which provides radio frequency shielding, and further allows for the maximization of the space in the inner area 20 of the enclosed structure 14 for the storage of endoscopes E.

With specific reference to FIGS. 1-4, and in some non-limiting embodiments or aspects, provided are filtered vents 44 having fans within and on a sidewall of the cabinet 10 to provide for clean air circulation within the cabinet 10 and outside the endoscopes E. The filtered vents 44 may also be positioned on the ceiling or floor of the cabinet. As discussed above, the endoscopes E are held securely, i.e., in a vertical manner, in the cabinet 10, which may reduce the chances of damaging the expensive endoscopes E, and which allows for efficient drying. The cabinet 10 may be manufactured from a secure and easy-to-clean material, and the support arrangements 22 can be manufactured from a non-abrading plastic. The asymmetric layout and positioning of the support arrangements 22 may permit the endoscopes E to be "pulled" into the hooks by gravity. Further, since the pitch is fixed, the endoscope E is prevented from swinging within the cabinet 10.

With specific reference to FIGS. 1-4, and in some non-limiting embodiments or aspects, the door 18 may at least partially be formed from glass 62 for allowing a person to view its contents without requiring access. Of course, if such visibility is not desired, the door 18 can be made from any suitable opaque material or structure. Still further, any of the portions of the walls 16 of the enclosed structure 14, including the top, floor, side, etc., may be shielded to prevent signals emitted in the inner area 20 from escaping the cabinet 10 (possibly causing interference with other devices and components).

With specific reference to FIGS. 1-4, and in some non-limiting embodiments or aspects, the cabinet 10 may further include a drying system made up of one or more drying manifolds 70a, 70b. A drying manifold 70a, 70b may include one or more air filters, fans, compressors, pumps, and/or microcontrollers for pulling in air, directly or indirectly via conduit, from either inside or outside the cabinet 10 and forcing the air through the channels of an endoscope E to promote efficient drying. The cabinet 10 may include a compressor 25 for providing an airflow to the drying manifolds 70a, 70b from inside/outside the cabinet 10. The compressor 25 may include a HEPA filter for purifying the airflow used to dry the interior channels of the endoscopes E. The compressor 25 may also be any sufficient fan, pump, or airflow mechanism to create an airflow. The compressor 25 is depicted as being located at the bottom of the cabinet 10, but the compressor 25 may be located elsewhere in or on the cabinet 10, or otherwise provided integrally with the drying manifolds 70a, 70b (as one or many compressors 25). A drying manifold 70a, 70b may be programmed and/or configured to be controlled by a local control device 30 to carry out a drying protocol for an endoscope E. A drying protocol may include the rules/parameters for the drying process of an endoscope E, which may include, but are not limited to, airflow duration, airflow temperature, airflow humidity, airflow speed, airflow pressure, airflow filtration level, maximum time allowed before reprocessing, and/or the like. Although FIGS. 1-4 depict some non-limiting embodiments or aspects having an upper drying manifold 70a and a lower drying manifold 70b, it will be appreciated that one or more manifolds may be employed in any position within the cabinet 10. It will also be appreciated that all or a part of the body of the manifolds 70a, 70b may be positioned outside the walls 16 of the cabinet 10.

With specific reference to FIGS. 1-4, and in some non-limiting embodiments or aspects, provided is an array of one or more upper airflow outputs 72, each for connection to a first end E1 of an endoscope E, and an array of one or more lower airflow outputs 74, each for connection to a second end E2 of an endoscope E. Each airflow output 72, 74 directs air from its associated drying manifold 70a, 70b and into a channel of an endoscope E via an airflow connection to the endoscope E. In the non-limiting embodiment depicted, each upper airflow output 72 is connected to the upper drying manifold 70a, and each lower airflow output 74 is connected to the lower drying manifold 70b. It will be appreciated that the airflow outputs 72, 74 may be connected to any number of same or different drying manifolds 70a, 70b within the cabinet 10. Each drying manifold 70a, 70b may include, for each airflow output 72, 74, a user control input 76, e.g., a button, a switch, a touchpad, and/or the like, for manually initiating, pausing, stopping, controlling, or modifying the drying protocol for an endoscope E connected to the manifold 70a, 70b via an airflow output 72, 74. Each manifold 70a, 70b may also include, for each airflow output 74, 76, one or more visual indicators 78, e.g., an LED, a screen, a timer display, and/or the like, to indicate one or more statuses of the drying protocol for a connected endoscope E. For example, the visual indicators 78 may include LED lights, wherein an LED light corresponding to an airflow output 72, 74 may glow red when the airflow connection to the endoscope E is faulty, or may glow green when the airflow connection to the endoscope E is properly established. In another example, the visual indicators 78 may include a timer display showing the length of time each endoscope E has been connected to a drying manifold 70a, 70b. It will be appreciated that many configurations are possible.

With specific reference to FIGS. 1-4, and in some non-limiting embodiments or aspects, the tracking system, using the signal receiving member 24 and the signal emitting members 12 on each endoscope E, may provide customized tracking and interaction vis-à-vis the drying system, which may include the drying manifolds 70a, 70b. As a user approaches the drying cabinet 10 with an endoscope E, or introduces an endoscope E into the inner space 20 of the drying cabinet 10, the signal emitting member 12 may be detected by the signal receiving member 24. The local computing device 30 (or a central computing device or controller) may determine, based at least partially on the signal received from the signal emitting member 12, an identifier of the introduced endoscope E. All or part of the signal may carry the identifier, or a token associated with an identifier. The signal may also be encrypted. The identifier may be an identifier for the signal emitting member 12 itself, which may be looked up in a database to determine further information, such as the type of endoscope E that the signal emitting member 12 is attached to, the drying protocol for the associated endoscope E, and/or the like. The identifier may also be an identifier for the endoscope E itself, which may provide more immediate determination of the endoscope E type and drying protocol. The identifier may also be an identifier for the drying protocol that is appropriate for the associated endoscope E. Many configurations are possible. Based at least partially on the identifier, the local computing device 30 (or a central computing device or controller) may determine the drying protocol for the endoscope E. For example, a drying protocol associated with the identifier may be determined from a lookup table in a communicatively connected database. Many configurations are possible.

With specific reference to FIGS. 1-4, and in some non-limiting embodiments or aspects, the local computing device 30 (or a central computing device or controller) may identify a specific support arrangement 22 in the cabinet 10 for the user to place the endoscope E on for storage and drying. The support arrangement 22 may be identified based on one or more parameters including, but not limited to, availability (based on a support arrangement 22 not already being occupied by an endoscope E), airflow output 72, 74 configuration (based on the type of connectors of the endoscope E and the types of connectors of the airflow outputs 72, 74 corresponding to the position of the support arrangement 22), drying protocol (based on the type of endoscope E and the configuration of the manifolds 70a, 70b and/or airflow outputs 72, 74), a predetermined/preset loading order (based on a user-input criteria for storage flow, e.g., load on farthest left hook available, load on nearest hook to most recent last entered endoscope E, load on hook farthest from other endoscopes E, etc.), and/or the like. More than one support arrangement 22 may be provided to accommodate two or more types of endoscopes E, based on support position (e.g., ceiling, wall, height from ground, etc.), position and configuration of airflow outputs 72, 74 (e.g., size of output, airflow rate of output, size of output connector, etc.), size and shape of the endoscope E, and the like. The local computing device 30 may matching endoscopes E with compatible support arrangements 22 based on an identifier of each signal emitting member 12 attached to each endoscope E. The local computing device 30 (or a central computing device or controller) may also determine a connection status indicative of whether the endoscope E has been properly connected to the airflow outputs 72, 74 associated with the identified support arrangement. The connection status may be determined by temporarily activating airflow at the upper airflow output 72 and the lower airflow output 74 and evaluating the air pressure of the connections. When an endoscope E is connected to an airflow output 72, 74, the air pressure required to create an airflow out of the airflow output 72, 74 would increase due to the length of endoscope E channel through which the airflow travels. A threshold air pressure may be predetermined by measuring air pressure at the airflow outputs 72, 74 when an endoscope E is verified to be properly connected. The threshold air pressure may also be set at an engineering factor above or below the average expected value of air pressure at an airflow output 72, 74. During use, the actual air pressure at the airflow outputs 72, 74 may be compared to the threshold air pressure, and if the actual air pressure for an airflow output 72, 74 is less than or equal to the threshold air pressure, then the system may alert the user that the connection is faulty. The alert may be created by a feedback device in the cabinet 10, and a feedback device may be visual (indicator lights, ceiling lights, display screens), auditory (speakers, vibrations), haptic (mechanical vibrations, pulses), and/or the like. It will be appreciated that many configurations are possible.

With specific reference to FIGS. 1-4, and in some non-limiting embodiments or aspects, if it is determined that the endoscope E has been properly connected to one or more required airflow outputs 72, 74, the local control device 30 (or a central computing device or controller) may initiate a drying process according to the drying protocol for the endoscope E by causing one or more of the drying manifolds 70a, 70b to activate an airflow from the one or more required airflow outputs 72, 74. The drying protocol may be initiated after it is determined that the user has closed a door 18 of the cabinet 10. The drying protocol may be held for initiation until it is determined that the door 18 has been closed and/or the locking mechanism 82 has been engaged. It will be appreciated that many configurations are possible.

With specific reference to FIGS. 1-4, and in some non-limiting embodiments or aspects, the cabinet 10 may run a full system scan for more than one endoscope E and determine the drying protocols for each endoscope E, particularly according to their position in the cabinet 10. For a cabinet 10 configured in a wider endoscope tracking system of other cabinets, storage arrangements, and/or reprocessing systems, additional antennas and computing devices may be positioned on other machines, storage devices, throughout the room, etc., to track the signal emitting member of an endoscope. Tracking may be coordinated through communication between multiple computing devices, or it may be managed by a central computing device. As such, location data (e.g., detected proximity to a known location, absolute coordinates or positioning, and/or the like) may be generated as a signal emitting member and, therefore, its associated endoscope, is moved through the storage and reprocessing environment(s). If the location data indicates a signal emitting member was detected at a reprocessing system prior to arriving for storage at the cabinet 10, the system may determine that the endoscope has been cleaned. If the location data does not include a detection at a reprocessing system after use of the endoscope and prior to arriving at the cabinet 10, the system may determine that the endoscope has not been cleaned. In response to determining that an endoscope has not been cleaned, a notification may be emitted at the drying cabinet, e.g., a warning displayed on a computer interface, a variation in the color or intensity of lighting elements, a sound or audio warning broadcast from speakers, and/or the like. If it is presumed or detected that an endoscope has been placed within the cabinet 10 and has not been cleaned, the locking mechanism 82 of the drying cabinet 10 may be engaged to prevent the cabinet 10 from being opened until a personnel can come and rectify the situation (e.g., remove all scopes, sterilize cabinet, reprocess scopes, etc.). Many configurations are possible.

With specific reference to FIGS. 1-4, the cabinet 10 may be accessed through the use of a PIN-number, a user account/password combination, validation of a user through the use of a radio frequency embedded identification card (typically HID or barcode), etc. Additionally, biometric identification, such as finger and/or thumb print, eye-iris and retina scanning, and similar authentication and authorization techniques and methodologies can be used. Further, the cabinet 10 may be equipped with a barcode reader for use in obtaining data, such as patient EMR or account numbers, which represent unique identification of the patient and/or the visit. Some or all of these data receiving and processing devices and components can interface with the local control device 30, as well as some other remote or centrally located control device. Still further, a local control device 30, or any of these other electrical components and data gathering devices, may be integrated with or otherwise interfaced with the hospital computer systems and network. The local control device 30 (or remotely-situated central computing device or controller) may allow the user to manage the system in process, such as through a visual display device 80. The visual display device 80 may be a touch screen for use in interacting with the cabinet 10, and may swing with the door 18 to provide full access to the inner area 20, as well as convenient access to the visual display device 80. As discussed, certain additional data receiving devices, such as in a RFID reader or a barcode reader, may be integrated with the cabinet 10 to permit only authorized access and/or beneficial functionality, e.g., patient selection. Certain standard "buttons" may be provided for anyone to appropriately locate a particular endoscope E or obtain an inventory of the cabinet 10, even if the user is not logged into the tracking system.

Accordingly, and in the foregoing non-limiting embodiments or aspects described above, the endoscope tracking system may include the appropriate computing devices and components in order to process signals emitted from a signal emitting member 12, data associated with these signals, etc., and this information is used to identify one or more attributes associated with a particular endoscope E. This data may also be transmitted by a local control device 30 of any number of cabinets 10. Of course, as discussed above, other components and portions of the overall process, e.g., the disinfection machines, the reprocessing station, etc., may also produce data that is tracked or otherwise captured and processed within the endoscope tracking system. Accordingly, the one or more attributes that are tracked and processed may include endoscope data, disinfection stage data, disinfection device data, damage data, cleaning data, use data, associated user/personnel data (e.g., which staff members have interacted with a scope), associated patient data (e.g., which patients have had procedures using the scope), location data, alert data, time data, or the like. Moreover, tracked endoscope E attributes may include any number of aspects about associated drying protocols and cleansing/reprocessing protocols, including: air pressure, temperature, humidity, time of entry, time of withdrawal, location of check-in, duration of processing/drying, duration of storage after drying, and/or the like. In this manner, meaningful scope history data can be produced through such integrated tracking systems, which is useful to prevent bacterial outbreaks/cross-contamination by identifying how contaminated scopes were used, to reduce/even out wear on scopes by identifying which scopes are being over/under-used, to identify which scopes have not been properly cleaned/dried or need to be reprocessed due to excess shelf-time, and to prevent inventory loss.

In some non-limiting embodiments or aspects, the endoscope tracking system may include a central control device that is in direct or indirect communication with the storage cabinets 10, the reprocessing station, the disinfection machines, directly with the signal emitting member 12, the signal receiving device 24, or any other component within the overall system and arrangement. Accordingly, it may be this central control device that is supportive of or enables the generation of the initial correlation between a specific signal emitting member 12 and a specific endoscope E.

Further, and within the context of the non-limiting embodiments or aspects of the endoscope tracking system, the local control device 30 may be in the form of a local computing device that is positioned on or near the cabinet 10, which is configured to communicate and control one or more of the components of the cabinet 10. In addition, the central control device may be in the form of a remote central control device that is in communication with the local computing device of each of the cabinets 10. Of course, this central control device may be local to one or more of the cabinets 10, and may constitute the primary controller to engage in the communication with and processing of signals derived from the signal emitting members 12 or other portions of the overall process and arrangement.

Although the disclosure has been described in detail for the purpose of illustration based on what is currently considered to be the most practical and preferred and non-limiting embodiments, it is to be understood that such detail is solely for that purpose and that the disclosure is not limited to the disclosed embodiments but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A computer-implemented method for tracking at least one endoscope in a forced-air drying cabinet comprising at least one compressor, at least one support arrangement, and an inner area accessible by at least one door, the method comprising:

receiving, with at least one processor, at least one signal from at least one signal emitting member attached to or associated with the at least one endoscope;

determining, with at least one processor and based at least partially on the at least one signal, at least one identifier of the at least one endoscope;

determining, with at least one processor, at least one drying protocol for the at least one endoscope based at least partially on the at least one identifier of the at least one endoscope, the at least one drying protocol comprising at least one of the following: at least one airflow duration, at least one airflow pressure, at least one airflow speed, at least one airflow temperature, at least one airflow humidity, or any combination thereof;

identifying, with at least one processor, the at least one support arrangement to support the at least one endoscope, the at least one support arrangement associated with at least one first airflow output and at least one second airflow output;

determining, with at least one processor, at least one connection status indicative of whether at least one first end of the at least one endoscope has been connected to the at least one first airflow output and at least one second end of the at least one endoscope has been connected to the at least one second airflow output; and in response to the at least one connection status indicating the at least one endoscope has been connected to the at least one first airflow output and the at least one second airflow output, initiating, with at least one processor, at least one drying process according to the at least one drying protocol for the at least one endoscope by causing the at least one compressor to create at least one airflow through the at least one endoscope from the at least one first airflow output, the at least one second airflow output, or a combination thereof.

2. The computer-implemented method of claim 1, further comprising:

receiving, with at least one processor, location data of the at least one signal emitting member associated with the at least one endoscope;

in response to the location data comprising data of at least one prior detection of the at least one signal emitting member at an endoscope reprocessing system immediately preceding receiving the at least one signal, determining, with at least one processor, that the at least one endoscope has been cleaned; and in response to the location data not comprising data of at least one prior detection of the at least one signal emitting member at an endoscope reprocessing system immediately preceding receiving the at least one signal, determining, with at least one processor, that the at least one endoscope has not been cleaned.

3. The computer-implemented method of claim 2, further comprising, in response to determining that the at least one endoscope was not cleaned, generating, with at least one processor, at least one warning notification at the forced-air drying cabinet.

4. The computer-implemented method of claim 3, further comprising, in response to determining that the least one endoscope was not cleaned, activating, with at least one processor, at least one locking mechanism of the forced-air drying cabinet to prevent the at least one door from being opened until it is unlocked by a personnel.

5. The computer-implemented method of claim 1, further comprising prior to initiating the at least one drying protocol for the at least one endoscope, verifying, with at least one processor, that the at least one door is closed.

6. The computer-implemented method of claim 5, further comprising, in response to determining that the at least one door is open:

generating, with at least one processor, at least one notification at the forced-air drying cabinet that the at least one door is open; and waiting to initiate, with at least one processor, the at least one drying protocol for the at least one endoscope until the at least one door is closed.

7. The computer-implemented method of claim 1, wherein the at least one support arrangement comprises at least two support arrangements of different configurations associated with at least two different types of endoscope, and wherein the identifying the at least one support arrangement is based at least partially on the at least one identifier of the at least one endoscope and further comprises determining, with at least one processor, a configuration of support arrangement required for the at least one endoscope.

8. The computer-implemented method of claim 1, wherein the at least one drying protocol comprises the at least one airflow duration, the method further comprising:

tracking, with at least one processor, at least one duration of the at least one endoscope being in the forced-air drying cabinet; and controlling, with at least one processor, at least one time display to provide at least one remaining drying time for the at least one endoscope based at least partially on the at least one airflow duration of the at least one drying protocol in relation to the at least one duration of the at least one endoscope being in the forced-air drying cabinet.

9. The computer-implemented method of claim 8, further comprising, in response to determining that the at least one duration of the at least one endoscope being in the forced-air drying cabinet satisfies at least one predetermined threshold for the at least one endoscope, generating, with at least one processor, at least one notification at the forced-air drying cabinet identifying the at least one endoscope as requiring reprocessing.

10. The computer-implemented method of claim 1, wherein the forced-air drying cabinet further comprises at least one visual indicator associated with the at least one support arrangement, the method further comprising:

in response to identifying the at least one support arrangement to support the at least one endoscope, controlling, with at least one processor, the at least one visual indicator associated with the at least one support arrangement to direct personnel attention to the at least one support arrangement.

11. The computer-implemented method of claim 10, wherein the determining the at least one connection status comprises evaluating, with at least one processor, at least one outlet air pressure at the at least one first airflow output associated with the at least one support arrangement identified to support the at least one endoscope and at the at least one second airflow output associated with the at least one support arrangement identified to support the at least one endoscope to at least one predetermined threshold.

12. The computer-implemented method of claim 11, further comprising, in response to determining that the at least one connection status of the at least one endoscope indicates that the at least one endoscope is not connected, controlling, with at least one processor, the at least one visual indicator associated with the at least one support arrangement to indicate that the at least one endoscope is not connected.

13. A system comprising:

a forced-air drying cabinet comprising at least one compressor, at least one support arrangement, at least one first airflow output and at least one second airflow output associated with the at least one support arrangement, and an inner area accessible by at least one door;

at least one signal emitting member associated with at least one endoscope;

at least one server computer comprising at least one processor, the at least one server computer configured to:

receive at least one signal from the at least one signal emitting member;

determine, based at least partially on the at least one signal, at least one identifier of the at least one endoscope;

determine at least one drying protocol for the at least one endoscope based at least partially on the at least one identifier of the at least one endoscope, the at least one drying protocol comprising at least one of the following: at least one airflow duration, at least one airflow pressure, at least one airflow speed, at least one airflow temperature, at least one airflow humidity, or any combination thereof;

identify the at least one support arrangement to support the at least one endoscope;

determine at least one connection status indicative of whether at least one first end of the at least one endoscope has been connected to the at least one first airflow output associated with the at least one support arrangement and at least one second end of the at least one endoscope has been connected to the at least one second airflow output associated with the at least one support arrangement; and in response to the at least one connection status indicating the at least one endoscope has been connected to the at least one first airflow output and the at least one second airflow output associated with the at least one support arrangement, initiate at least one drying process according to the at least one drying protocol for the at least one endoscope by causing the at least one compressor to create at least one airflow through the at least one endoscope from the at least one first airflow output, the at least one second airflow output, or a combination thereof.

14. The system of claim 13, wherein the at least one server computer is further configured to:

receive location data of the at least one signal emitting member associated with the at least one endoscope;

in response to the location data comprising data of at least one prior detection of the at least one signal emitting member associated with the at least one endoscope at an endoscope reprocessing system immediately preceding receiving the at least one signal, determine that the at least one endoscope has been cleaned; and in response to the location data not comprising data of at least one prior detection of the at least one signal emitting member associated with the at least one endoscope at an endoscope reprocessing system immediately preceding receiving the at least one signal, determine that the at least one endoscope has not been cleaned.

15. The system of claim 13, wherein the at least one drying protocol comprises the at least one airflow duration, and wherein the at least one server computer is further configured to:

track at least one duration of the at least one endoscope being in the forced-air drying cabinet; and control at least one time display to provide at least one remaining drying time for the at least one endoscope based at least partially on the at least one airflow duration of the at least one drying protocol in relation to the at least one duration of the at least one endoscope being in the forced-air drying cabinet.

16. The system of claim 15, wherein the at least one server computer is further configured to, in response to determining that the at least one duration of the at least one endoscope being in the forced-air drying cabinet satisfies at least one predetermined threshold for the at least one endoscope, generate at least one notification at the forced-air drying cabinet identifying the at least one endoscope as requiring reprocessing.

17. A computer program product for tracking at least one endoscope in a forced-air drying cabinet comprising at least one compressor, at least one support arrangement, and an inner area accessible by at least one door, the computer program product comprising at least one non-transitory computer-readable medium including program instructions that, when executed by at least one processor, cause the at least one processor to:
  receive at least one signal from at least one signal emitting member associated with the at least one endoscope;
  determine, based at least partially on the at least one signal, at least one identifier of the at least one endoscope;
  determine at least one drying protocol for the at least one endoscope based at least partially on the at least one identifier of the at least one endoscope, the at least one drying protocol comprising at least one of the following: at least one airflow duration, at least one airflow pressure, at least one airflow speed, at least one airflow temperature, at least one airflow humidity, or any combination thereof;
  identify the at least one support arrangement to support the at least one endoscope, the at least one support arrangement associated with at least one first airflow output and at least one second airflow output;
  determine at least one connection status indicative of whether at least one first end of the at least one endoscope has been connected to the at least one first airflow output and at least one second end of the at least one endoscope has been connected to the at least one second airflow output; and
  in response to the at least one connection status indicating the at least one endoscope has been connected to the at least one first airflow output and the at least one second airflow output, initiate at least one drying process according to the at least one drying protocol for the at least one endoscope by causing the at least one compressor to create at least one airflow through the at least one endoscope from the at least one first airflow output, the at least one second airflow output, or a combination thereof.

18. The computer program product of claim 17, wherein the program instructions further cause the at least one processor to:
  receive location data of the at least one signal emitting member associated with the at least one endoscope;
  in response to the location data comprising data of at least one prior detection of the at least one signal emitting member associated with the at least one endoscope at an endoscope reprocessing system immediately preceding receiving the at least one signal, determine that the at least one endoscope has been cleaned; and
  in response to the location data not comprising data of at least one prior detection of the at least one signal emitting member associated with the at least one endoscope at an endoscope reprocessing system immediately preceding receiving the at least one signal, determine that the at least one endoscope has not been cleaned.

19. The computer program product of claim 17, wherein the at least one drying protocol comprises the at least one airflow duration, and wherein the program instructions further cause the at least one processor to:
  track at least one duration of the at least one endoscope being in the forced-air drying cabinet; and
  control at least one time display to provide at least one remaining drying time for the at least one endoscope based at least partially on the at least one airflow duration of the at least one drying protocol in relation to the at least one duration of the at least one endoscope being in the forced-air drying cabinet.

20. The computer program product of claim 19, wherein the program instructions further cause the at least one processor to, in response to determining that the at least one duration of the at least one endoscope being in the forced-air drying cabinet satisfies at least one predetermined threshold for the at least one endoscope, generate at least one notification at the forced-air drying cabinet identifying the at least one endoscope as requiring reprocessing.

* * * * *